United States Patent [19]

Carter, Jr. et al.

[11] Patent Number: 5,300,750
[45] Date of Patent: Apr. 5, 1994

[54] THERMAL INDUCTION HEATER

[75] Inventors: Philip S. Carter, Jr.; Michael Hodges; John P. Ekstrand; Andrew Tomlinson, all of Palo Alto, Calif.

[73] Assignee: Metcal, Inc., Menlo Park, Calif.

[21] Appl. No.: 774,243

[22] Filed: Oct. 10, 1991

Related U.S. Application Data

[63] Continuation-in-part of Ser. No. 442,653, Nov. 29, 1989, which is a continuation-in-part of Ser. No. 270,843, Nov. 14, 1988, abandoned, which is a continuation-in-part of Ser. No. 169,027, Mar. 16, 1988, abandoned.

[51] Int. Cl.$^5$ ............................................... H05B 6/02
[52] U.S. Cl. ..................................... 219/605; 606/28; 219/636; 219/609
[58] Field of Search ................... 219/10.491, 10.55 E, 219/9.5, 10.77, 10.73, 10.79, 10.67, 10.75, 10.493, 548, 553, 528, 545, 488, 489, 494; 99/DIG. 14; 606/28

[56] References Cited

U.S. PATENT DOCUMENTS

| | | | |
|---|---|---|---|
| 1,807,105 | 5/1931 | Schliephake | 128/804 |
| 3,569,672 | 3/1971 | Hurko | 219/464 |
| 3,653,385 | 4/1972 | Burton | 600/10 X |
| 4,256,945 | 3/1981 | Carter et al. | 219/10.75 |
| 4,309,596 | 1/1982 | Crowley | 219/549 |
| 4,354,082 | 10/1982 | Tellert et al. | 219/10.49 R |
| 4,545,368 | 10/1985 | Rand et al. | 600/13 X |
| 4,617,456 | 10/1986 | Richards et al. | 219/523 |
| 4,701,587 | 10/1987 | Carter et al. | 219/233 X |
| 4,733,059 | 3/1988 | Goss et al. | 219/548 |
| 4,807,620 | 2/1989 | Strul et al. | 606/28 |
| 4,876,440 | 10/1989 | Kamath et al. | 219/548 |
| 4,972,459 | 11/1990 | Sommer | 378/193 |
| 5,060,287 | 10/1991 | Van Egmond | 392/301 |
| 5,061,835 | 10/1991 | Iguchi | 219/10.79 |

FOREIGN PATENT DOCUMENTS

| | | | |
|---|---|---|---|
| 1284528 | 12/1968 | Fed. Rep. of Germany | 600/10 |
| WO81/02833 | 10/1981 | PCT Int'l Appl. | 128/804 |
| 1037226 | 8/1983 | U.S.S.R. | |

OTHER PUBLICATIONS

Sabbagh, Hr., "A Model of Eddy-Current Probes with Ferrite Cores", IEEE Transactions on Magnetics, vol. Mag-23, No. 2, pp. 1888-1904, Mar. 1987.

Matsuki et al, "An Optimum Design of a Soft Heating System for Local Hyperthermia, IEEE Transactions on Magnetics", vol. Mag-23, No. 5, pp. 2440-2442, Sep. 1987.

Thackray et al, "Indirect Heating Source for Treatment of Malignant Brain Tumors", Electrocomponent Science and Techhnology, vol. 1, No. 2, pp. 91-96, Dec. 1974.

Matsuki et al, "High Qyality Soft Heating Method Utilizing Temperature Dependence of Permeability and Core Loss of Low Curie Temperature Ferrite", IEEE Transactions on Magnetics, vol. Mag-21, No. 5, pp. 1927-1929 Sep. 1985.

Brezovich et al, "Effect of Catheters on the Performance of Self-Regulating Thermoseeds", IEEE Ninth Annual Conference of the Engineering in the Medicine and Biology Society, 1987, vol. 3, pp. 1629-1630.

Lilly et al, "Hyperthermia Induction with Thermally Self-Regulated Ferromagnetic Implants", Radiology, vol. 154, No. 1, p. 243, Jan. 1985.

Leonard et al, "Thermoelectric Power of Gold-Silver Alloy Films", 1976, Dept. of Elec. Eng., Southern Methodist University.

Atkinson et al, "Usable Frequencies in Hyperthermia with Thermal Seeds", IEEE Transactions on Biomedical Engineering, vol. BME-31, pp. 70-75, Jan. 1984.

Brezovich, "Low Frequency Hyperthermia: Capacitive and Ferromagnetic Thermoseed Methods", after Jan. 1987.

*Primary Examiner*—Bruce A. Reynolds
*Assistant Examiner*—Tu Hoang
*Attorney, Agent, or Firm*—Howard L. Rose

[57] ABSTRACT

A heater employs a ferromagnetic or like material heated by a varying magnetic field to heat the ferromagnetic material wherein the ferromagnetic material has a large cross-section comprised of many members of small cross-section insulated from one another and wherein for medical applications each member may be surrounded by a heat conductive electrically conductive coating.

18 Claims, 4 Drawing Sheets

THERMAL INDUCTION HEATER

RELATED APPLICATIONS

This application is a continuation-in-part of application Ser. No. 07/442,653 filed Nov. 29, 1989, by Philip S. Carter, Jr. which was a continuation-in-part application Ser. No. 07/270,843 filed Nov. 14, 1988, now abandoned, which was a continuation-in-part of application Ser. No. 169,027 filed Mar. 16, 1988, now abandoned, all entitled Thermal Seed for Treatment of Tumors.

FIELD OF INVENTION

The present invention relates to heaters employing magnetic flux energized ferromagnetic or other high magnetic permeability (high mu) materials and more particularly to heaters employing structures employing laminated layers or bundles of thin fibers of high mu materials.

Reference is made to ferromagnetic materials, high mu materials or magnetically permeable materials or the magnetic permeability ($\mu$) of materials. These materials provide for a high degree of concentration of magnetic flux in them as long as they are below their effective Curie temperatures. The flux produces eddy current and hysteresis losses as well as resistive losses. Such materials may be principally ferromagnetic or ferrimagnetic but other materials whose degree of magnetic permeability varies with temperature are also available. Throughout this specification these materials shall be collectively referred to as "ferromagnetic" materials.

Although the present invention is described as applicable to apparatus for producing lesions in brain tumors (thermal seeds) the structure of the embodiment of FIG. 4 in particular but not exclusively is also applicable to heaters for other purposes such as griddles, stoves and other alternating or fluctuating magnetic field activated heaters.

BACKGROUND OF INVENTION

In copending U.S. application Ser. No. 07/442,653 filed Nov. 29, 1989 for Thermal Seed For Treatment of Tumors and assigned to the same assignee as the present invention, the disclosure which is incorporated herein in its entirety by reference, there is described a thermal seed for implantation in a tumor, for instance a brain tumor, wherein the thermal seed incorporating a ferromagnetic material is excited by an externally developed, varying magnetic field. As discussed in the aforesaid application there are several articles and a patent describing the work of various researchers in the field. Reference is made to Burton, U.S. Pat. No. 3,653,385; Matsuki et al's article in *IEEE Transactions on Magnetics*, Vol. Mag-21, No. 5, September 1985; Matsuki et al's article in *IEEE Transactions on Magnetics*, Vol. Mag-23, No. 5, September 1987 and German Patent Application No. P12-84-528.2 of Dr. Forster published Dec. 5, 1968. All of these materials are discussed in some detail in the aforesaid Carter et al. application.

In accordance with the aforesaid Carter et al. application, the length to diameter ratio of the seed should be at least 10 and preferably 20 to minimize demagnetizing effects that reduce the permeability of the ferromagnetic material to a great extent, as much as 8 times. Further the application teaches the use of a conductive coating of bio-compatible material over substantially the entire outer surface of the seed to produce maximum heating of the seed and reduce biocontamination of adjacent tissues.

In the aforesaid device as applied to a practical structure; the larger diameter seed obviously intercepts a larger proportion of the magnetic flux than a small seed but also increases the deleterious demagnetizing effects and deleterious eddy current effects. Thus, with the large diameter seed, it is not possible for the seed to be fully penetrated by the flux and thus is not highly efficient.

OBJECTS OF THE INVENTION

It is an object of the present invention to provide a highly efficient, temperature stable large diameter heater employing curie temperature regulation wherein a ferromagnetic material is excited by a varying magnetic flux.

It is another object of the present invention to provide a highly efficient temperature stable heater employing a plurality of ferromagnetic elements of small cross-sectional area from another.

It is still another object of the present invention to provide a relatively large diameter heater of ferromagnetic material in which such material is fully penetrated by an exciting, varying magnetic flux.

Yet another object of the present invention is to provide ferromagnetic material of sufficiently small cross-sectional area to greatly reduce eddy currents relative to prior art devices.

BRIEF DESCRIPTION OF THE PRESENT INVENTION

In accordance with the present invention, there is provided a relatively large cross-sectional area heater employing a plurality of braided, twisted or laminated ferromagnetic members, each of a cross-section area such as to be fully penetrated by varying magnetic flux and to produce very little eddy currents and of a length to cross-sectional area ratio such as to reduce demagnetizing effects to acceptable levels.

If the heater is to be employed for insertion into the human body each ferromagnetic member is often encapsulated within a bio-compatible (inert) conductive covering such as gold, silver, etc. Alternatively, the entire assembly may be encapsulated within a single bio-compatible metal. If the heater is to be employed for non-therapeutic purposes, a bio-compatible coating is not as important, but a single conductive coating such as copper, aluminum, etc. may be employed. Also in such applications there is greater flexibility of geometry, the invasive device usually being cylindrical using cylindrical ferromagnetic fibers while for other uses the individual elements and the overall device may be cylindrical, a solid rectangle, a square or other suitable shapes.

As a result of such construction, a large diameter device is achieved but the desired length to cross-sectional area ratio and complete penetration of the fibers or layers by the magnetic flux is achieved thus providing a device of greatly enhanced efficiency.

In all systems efficiency is always an important concern but in a thermal seed high efficiency is extremely important since the heating produced in adjacent tissues by the electromagnetic field required to raise the seed to its Curie temperature can be detrimental to healthy tissues adjacent to the area to be treated and a material reduction in such energy is highly desirable.

DETAILED DESCRIPTION OF THE PRESENT INVENTION

Figure 1:
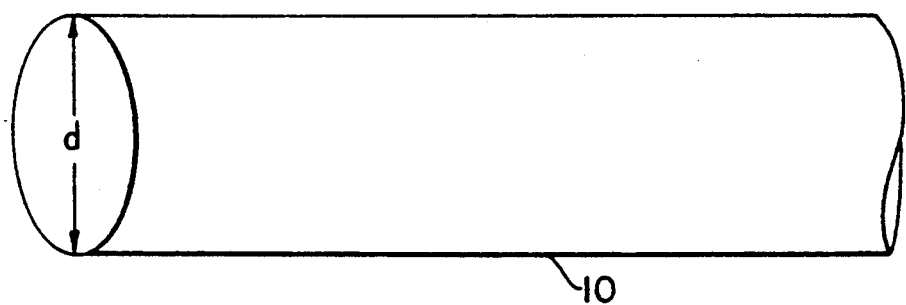
FIG. 1 is a perspective view of a standard fiber according to the prior art.
Figure 4:
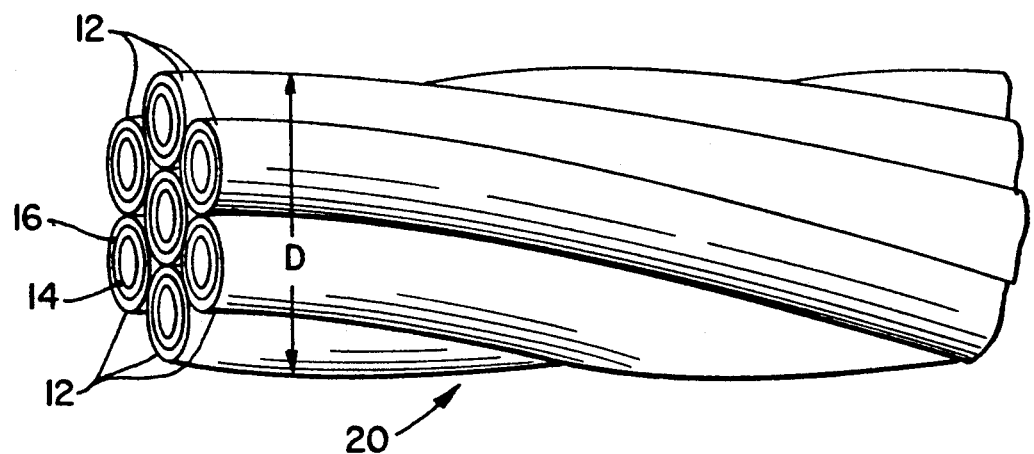
FIG. 4 is a view in perspective of a thermal seed comprising a bundle of ferromagnetic fibers.

Referring specifically to FIG. 4 of the accompanying drawings a number of discrete strands 2, 4, 6, . . . , 14 with an overall diameter D, about 1 mm, the same as that of a single prior art solid seed, provide a better penetration of the magnetic field into the seed and results in higher generated power for most values of $\mu$ relative to a solid seed. Each strand may be substantially encapsulated, as disclosed in the aforesaid Carter et al. application, in a bio-compatible conductive material 14 such as gold, silver or the like. In some instances it may be desirable to surround each strand with a heat conductive electrical insulator 16. Such may be desirable where the area of contact between adjacent strands may be larger but if small (tangential only) such insulation is not normally necessary. The strands may be braided or twisted within the bundle. The form of the power-temperature characteristic relative to a solid heater is altered so that the sharpness of the high temperature cutoff is improved and may be varied between the square and the square root of the function of $\mu$.

The analysis resulting in the following equations and the tests conducted that resulted in the graphs of FIGS. 2 and 3 were made with fibers that were not covered with a conductive material. The improvements over the prior art single fiber are quite pronounced even without the added effect of fully conductively coated fibers.

Relative to operation of this type of Curie point heater, as temperature increases, the generated power falls, since it is a function of the magnetic property $\mu$ which approaches one as the Curie temperature is approached. This function takes the form of a modification $\mu'$ of the magnetic property $\mu$ of the seed, namely:

$$\mu'/\mu = (2/A) \cdot \{ber(A) \cdot bei'(A) - bei(A) \cdot ber'(A)\}/\{ber^2(A) + bei^2(A)\} \quad (1)$$

where ber and bei are Bessel functions and A is defined by $A = \sqrt{\pi d(2\mu f/\rho)}$, d is the wire diameter, f the magnetic field frequency and $\rho$ the electrical resistivity of the wire. This equation is greatly simplified in the cases where A<1 (flux penetration is complete, the low frequency case) or A>>1 (flux penetration of surface only, the high frequency case). In the former case the power induced per unit volume is:

$$P = (\pi d \mu H f)^2 / 16\rho \quad (2)$$

where H is the magnetic field intensity. For the high frequency case the power is:

$$P = \{H^2 \sqrt{\mu \rho f}\}/4\pi d \quad (3)$$

Considering the case where frequency, resistivity, wire diameter and magnetic field are all held constant, it can be seen that in the low frequency case power is proportional to $\mu^2$, whereas in the high frequency case power is proportional to $\sqrt{\mu}$. In order to obtain the highest degree of control of temperature through the decrease of $\mu$ as the effective Curie temperature is approached, the system should be operated in the low frequency range, where power has the strongest dependence on $\mu$. If the frequency, field and resistivity are held constant, the wire diameter may be adjusted to insure that for all temperatures of interest for ferromagnetic hyperthermia, operation occurs in the low frequency case. The alloys that have effective Curie temperatures in the range of interest have resistivities of 55 to 85 microohm cm. Taking 100 kHz as a typical operating low frequency at a field of 2000 A/m, the limit of low frequency operation for a $\mu$ of 100 is a seed having a diameter of about 0.25 mm (0.010 inch).

Figure 2:
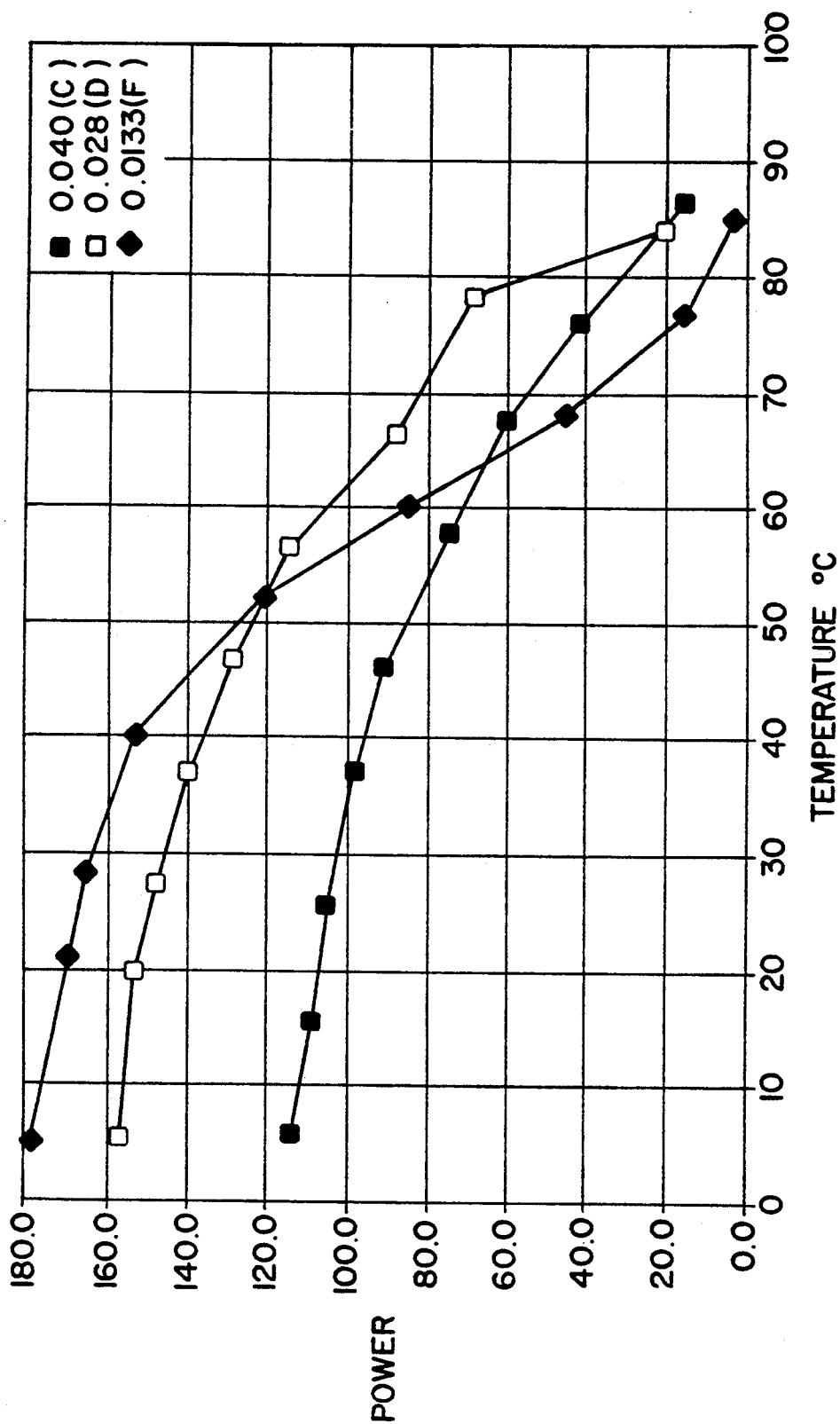
FIG. 2 is a graph of power per cubic centimeter of a thermal seed versus temperature for three different diameter ferromagnetic strands.
Figure 3:
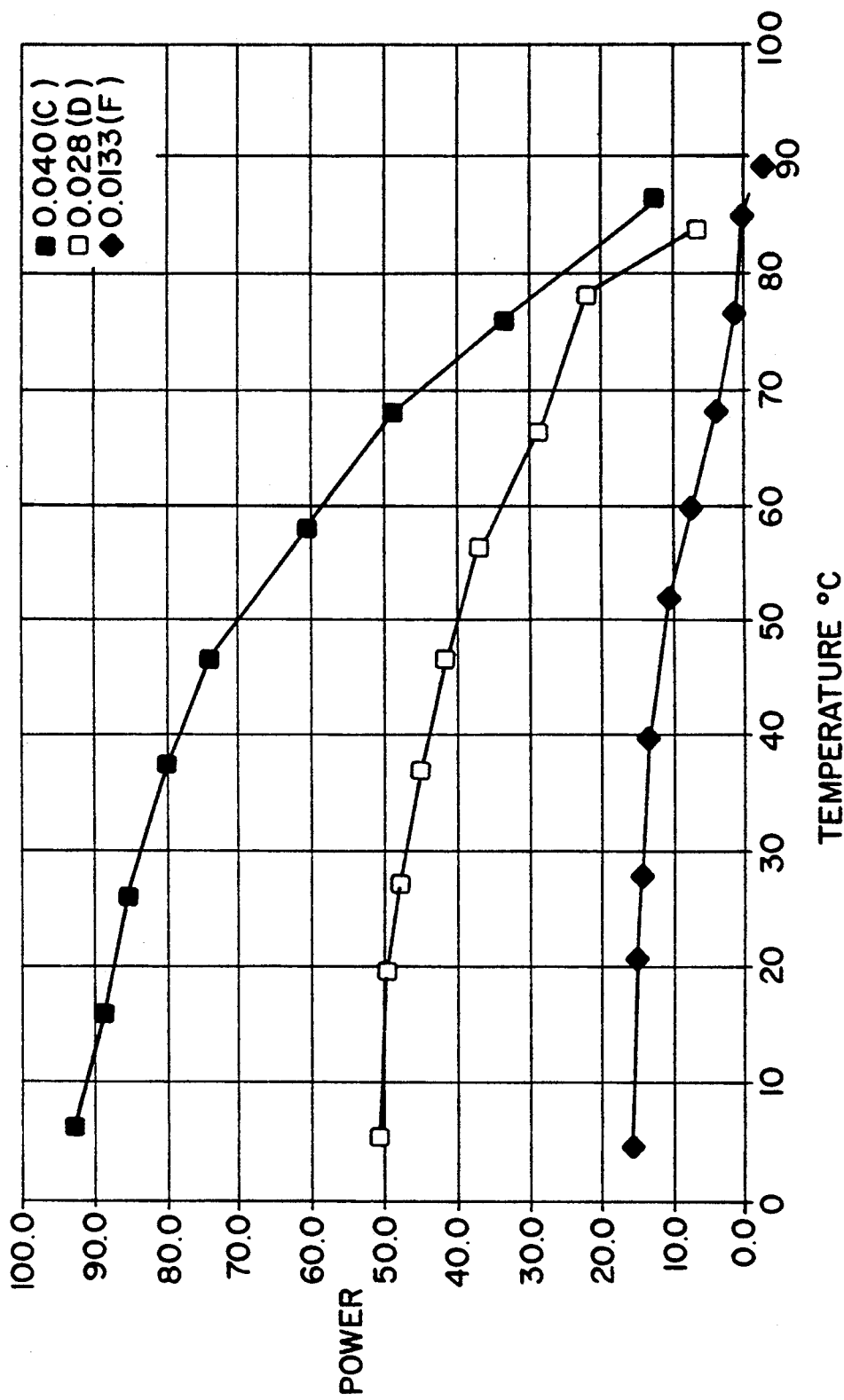
FIG. 3 is a graph of power per meter of seed versus temperature for three different diameters of a strand.

The above effect is shown in FIG. 2 for seeds of 31% nickel, 69% iron which have been annealed at 750° C. The three plotted curves, as shown by the legend, are for single strands of seeds of respective diameter 0.040 inch (1.00 mm), 0.028 inch (0.71 mm), and 0.0133 inch (0.34 mm). The data was obtained by mounting the seeds in a stream of water the temperature of which could be varied and measured. The seeds were simultaneously subjected to a known magnetic field, generated by a coil surrounding the seeds. The power absorbed by the seeds (vertical axis) was measured by taking the difference between the power required to drive the coil at a particular current with and without the seeds present. The power data has been normalized to the power generated by one milliliter of seed material to facilitate comparison of generated power on a volumetric basis. It can be seen that at 40° C. the power required per unit volume is greater for the 0.0133 inch diameter seeds than for either of the larger diameters. Also and more importantly the power is declining more rapidly as a function of temperature for the smaller diameter seeds thereby giving a sharper regulation effect. If this data is plotted instead for a unit length of seed as in FIG. 3, it is seen that the total power needed for heating the small diameter seeds to a given temperature is much less. The power can be increased by the use of a greater number of strands. Bearing in mind the need for these seeds to be implanted surgically, it is advantageous to make them into bundles by braiding or stranding them into groups (as in FIG. 4) for simultaneous multiple implanting.

Referring specifically to FIG. 4 of the accompanying drawing, individual strands 2, 4, 6, etc. of ferromagnetic material are preferably, but not necessarily, coated with a non-magnetic electrically conductive coating 14 as one construction to achieve the results set forth in the aforesaid Carter et al. application. A layer 16 of electrical insulation may be applied over each strand and the strands bundled by twisting or pigtailing. If the device is to be used as a thermal seed for insertion into a patient's body, the layer of electrical insulation must be bio-compatible. Teflon is a suitable insulator for this purpose if such is used.

In the prior Carter et al. application discussed above, the conductive coating, being the outmost coating, had to be bio-compatible. In the present application if the outer coating of insulation is bio-compatible, the conductive coating may be any conductive material that will not migrate through the insulating coating. Copper is such a material.

Further the very small diameter of the individually coated strands insures an excellent length to diameter ratio preferably of 20 or more thus readily maintaining the effective permeability in the region of 100 in spite of the demagnetizing effects of such structures. A ratio of 10:1 may also be employed but the results are not as satisfactory as with higher ratios. Demagnetizing effects are further greatly reduced in accordance with the present invention as a result of the significant reduction of eddy currents due to the small size of the elements.

The total effect of such a structure is to achieve greatly increased efficiency relative to a unitary structure as a result of provision of a large diameter seed, complete penetration of the ferromagnetic strands by the magnetic flux and reduced demagnetizing effects by achieving large length to diameter ratios and reduced eddy currents. In addition the use of the small diameter strands rather than a solid core allows the use of higher frequencies beyond the frequency at which the strand dimensions are greater than a couple of skin depths;

$$S.D. = 5030 \sqrt{\frac{\rho}{\mu f}} \text{ cm}$$

where $\rho$ is resistivity. Thus the range of available apparatus, power supplies, coils, etc. is increased.

Figure 5:
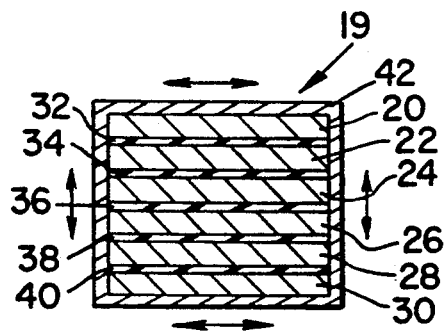
FIG. 5 is an end view of a laminated heater employing rectangularly shaped layers of ferromagnetic material.
Figure 6:
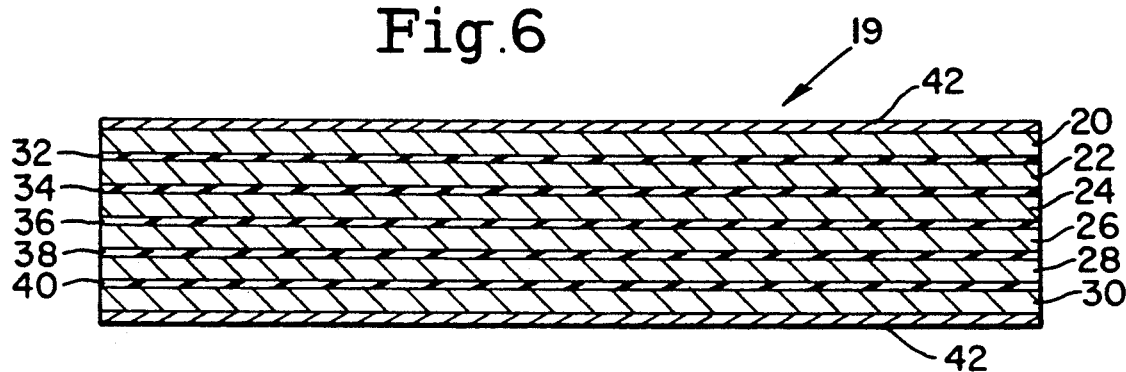
FIG. 6 is a side view of the structure of FIG. 5.

Referring now to FIGS. 5 and 6 there is illustrated an embodiment of the present invention which may be used for body implant but which as a result of its shape may be employed in numerous other environments.

The structure includes a core 19 of thin elongated, laminated bars, rods, layers 20, 22, 24, 26, 28 and 30, etc. rectangular in cross-section, for instance, and stacked to provide a desired overall shape in cross-section, substantially square in FIG. 5. The layers are of ferromagnetic material of desired Curie temperature preferably electrically insulated from one another by layers 32, 34, 36, 38 and 40 of thermally conductive material such as boron nitride. The entire structure is surrounded by an electrically and heat conductive layer 42 to provide a current flow path about the core 19. The very thin layers inhibit eddy currents and are thin enough to permit complete penetration of such layer by magnetic flux. The outer conductive layer provides the performance enhancement as set forth in the aforesaid application.

Figure 7:
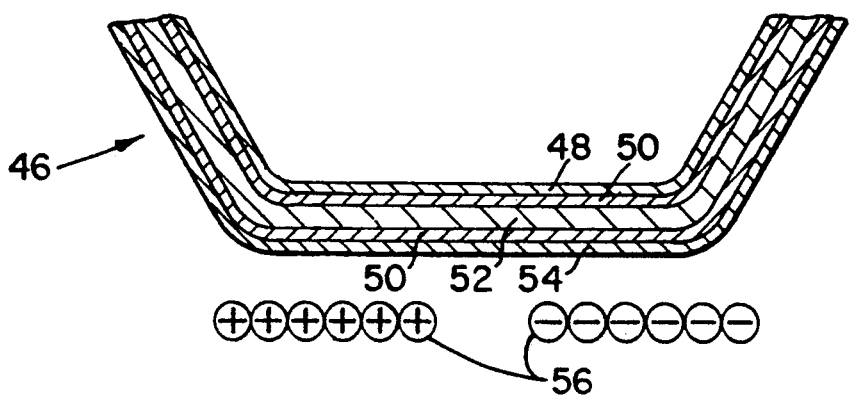
FIG. 7 is a section of view of a cooking pot employing the present invention.

Referring to FIG. 7 of the accompanying drawings, there is illustrated an induction cook pot 46 employing the structure of FIGS. 4 and 5 hereof. The pot comprises a non-magnetic stainless steel exterior layer 48, a resistive heating layer 50 for instance, copper, that surrounds a magnetic layer 52 that is constructed in accordance with the structure of FIGS. 4 and 5 and 6. The bottom or last layer 54 is non-magnetic stainless steel and may be a continuation of the layer 48 to provide an outer covering for the pot. The pot 46 is adapted to be disposed on but preferably slightly above an induction coil 56.

The pot 46 thus takes advantage of the efficiency provided by the concepts of the present invention.

Preferably the coil or coils are energized by a constant current so that as the ferromagnetic material approaches its effective Curie temperature the concentration of flux coupled to the seed is greatly reduced and thus so is the resistance reflected back into the coil. In consequence the standard power equation $P=I^2R$, becomes $P=KR$ where $K=2$.

The term "effective Curie temperature" is the temperature at which a material becomes, for purposes of this invention, essentially non-magnetic. Such temperature may be as little as 1° C. or as much as 100° C. less than absolute Curie temperature depending upon the material employed.

When the magnetic material approaches effective Curie temperature, R in the above equation is greatly reduced and thus the heat generated in the seed is reduced as a relatively linear function of the resistance reflected in the coil.

More specifically, the induction coil(s) is supplied with a constant alternating current to maintain uniform response to the energy output. The more uniform the current the better the temperature regulation. For the sake of analysis the seeds are considered to reflect resistance into the coils and under these circumstances the regulation is governed by the equation $$\frac{\Delta |I|}{|I|} < -\frac{1}{2} \frac{\Delta |R|}{|R|}$$

where $|I|$ is current and $|R|$ is the reflected resistance. If the current is held constant regulation is good. If the current is permitted to rise, the regulation becomes poorer as the value of the left side of the equation approaches the right side and the system fails if the value of the left side of the equation exceeds the value of the right side.

It should be noted that in all embodiments of the present invention a conductive sheath as provided in Carter et al.'s aforesaid application may be employed with the salutary effects as recited therein.

Many variations and modifications of the abovedescribed embodiments are within the ordinary skill of the skilled artisan in this art, without departing from the scope of the invention. Accordingly, those modifications and embodiments are intended to fall within the scope of the invention as defined by the following claims.

We claim:

1. An induction heater adapted to be heated in response to a linking fluctuating magnetic flux comprising a large cross-sectional feromagnetic core,
said core comprised of a plurality of ferromagnetic members of a cross-sectional area such that at a frequency of fluctuations of the magnetic flux the magnetic flux penetrates approximately to a center of each of said members.

2. An induction heater according to claim 1, further comprising
conductive means enclosing and in contact with said members and in which electrical currents are generated.

3. An induction heater according to claim 1, wherein each said member is substantially covered by a conductive means.

4. An induction heater according to claim 3, wherein said conductive means is bio-compatible.

5. An induction heater according to claim 3, wherein each said conductive means is covered by an electrical insulation layer.

6. An induction heater according to claim 5, wherein said insulating coating is bio-compatible.

7. An induction heater according to claim 1, wherein said core is enclosed within a single conductive layer.

8. An induction heater according to claim 1 or claim 2 or claim 3 or claim 4, wherein
each said member has a ratio of length to cross-section dimensions at least equal to 10.

9. An induction heater according to claim 1 or claim 2 or claim 3 wherein
each said member is long and thin.

10. An induction heater according to claim 9, wherein said members are braided.

11. An induction heater according to claim 9, wherein said members are twisted.

12. An induction heater according to claim 8, wherein said members are thin rectangles.

13. An induction heater according to claim 8, wherein said members are thin, and said members are covered with an electrically conductive, non-magnetic coating.

14. An induction heater according to claim 1 wherein said ferromagnetic material has an effective Curie temperature at a safe temperature relative to a material to be treated.

15. An induction heater according to claim 13, further comprising
a layer of heat conductive, electrical, non-magnetic insulation between each of said members.

16. An induction heater according to claim 13, further comprising
an electrically conductive coating surrounding said members.

17. An induction heater according to claim 13, further comprising
an electrically conductive covering over each of said ferromagnetic members.

18. An induction heater according to claim 16 wherein
said electrically conductive coating is comprised of said outer and inner layers.

* * * * *